(12) United States Patent
Lin et al.

(10) Patent No.: US 10,912,948 B2
(45) Date of Patent: Feb. 9, 2021

(54) COMPOSITE INTELLIGENT BIOLOGICAL PHOTOTHERAPY DEVICE

(71) Applicant: National Applied Research Laboratories, Taipei (TW)

(72) Inventors: Yi-Cheng Lin, Taipei (TW); Hsin-Yi Tsai, Taipei (TW); Min-Wei Hung, Taipei (TW); Kuo-Cheng Huang, Taipei (TW); Hsin-Su Yu, Taipei (TW); Chiou-Lian Lai, Taipei (TW); Chung-Yao Hsu, Taipei (TW); Chao-Hung Cheng, Taipei (TW); Li-Wei Kuo, Taipei (TW); Hung-Che Chiang, Taipei (TW); Chih-Yi Yang, Taipei (TW)

(73) Assignee: NATIONAL APPLIED RESEARCH LABORATORIES, Taipei (TW)

( * ) Notice: Subject to any disclaimer, the term of this patent is extended or adjusted under 35 U.S.C. 154(b) by 239 days.

(21) Appl. No.: 15/944,789

(22) Filed: Apr. 4, 2018

(65) Prior Publication Data

US 2019/0111277 A1 Apr. 18, 2019

(30) Foreign Application Priority Data

Oct. 13, 2017 (TW) .............................. 106135170 A (51) Int. Cl.
*A61N 5/06* (2006.01)

(52) U.S. Cl.
CPC ......... *A61N 5/0613* (2013.01); *A61N 5/0618* (2013.01); *A61N 2005/0626* (2013.01); *A61N 2005/0634* (2013.01); *A61N 2005/0642* (2013.01); *A61N 2005/0651* (2013.01);
(Continued)

(58) Field of Classification Search
CPC ................ A61N 5/0613; A61N 5/0618; A61N 2005/0642; A61N 2005/0634; A61N 2005/0652; A61N 2005/0655; A61N 2005/0663; A61N 2005/0626; A61N 2005/0651
See application file for complete search history.

(56) References Cited

U.S. PATENT DOCUMENTS

2017/0246474 A1 8/2017 Schanze
2017/0252442 A1 9/2017 Fang et al.

FOREIGN PATENT DOCUMENTS

TW M483709 U 8/2014
TW I598127 B 9/2017

*Primary Examiner* — Mark Bockelman
(74) *Attorney, Agent, or Firm* — Cheng-Ju Chiang (57) ABSTRACT

The present invention provides a composite intelligent biological phototherapy device including a base structure, a plurality of white light fluorescent tubes arranged side by side on the base structure, a plurality of LEDs disposed between the white light fluorescent tubes, a housing having an opening and configured to accommodate the base structure and the white light fluorescent tubes and the LEDs thereon, a light-transmittable plate disposed on the housing corresponding to the opening, and an control module configured to respectively control the white light fluorescent tubes and the LEDs. The base structure includes a plurality of sections, and each of the sections has a first surface facing the light-transmittable plate. The white light fluorescent tubes and the LEDs are provided on the first surfaces, and the sections are bent relative to each other so an angle between the first surfaces of adjacent sections is less than 180 degrees.

17 Claims, 5 Drawing Sheets

(52) U.S. Cl.
CPC ............... *A61N 2005/0652* (2013.01); *A61N 2005/0655* (2013.01); *A61N 2005/0663* (2013.01)

COMPOSITE INTELLIGENT BIOLOGICAL PHOTOTHERAPY DEVICE

CROSS REFERENCE AND PRIORITY

The present application claims benefit and priority from Taiwan Application No. 106135170, filed Oct. 13, 2017, which was entitled "COMPOSITE INTELLIGENT BIOLOGICAL PHOTOTHERAPY DEVICE". The entire disclosure of which is hereby incorporated by reference as if fully set forth herein.

FIELD OF INVENTION

This invention generally relates to a composite intelligent biological phototherapy device. Specifically, the present invention relates to a composite intelligent biological phototherapy device comprising fluorescent light sources with high color rendering index and functional LED light sources.

BACKGROUND

Recently, methods and effects of adjusting factors associated with biological rhythms, such as sleep cycles, changes in body temperature and melatonin, have drawn increasing attention. Further, since the hypothalamus in the brain is involved in the regulation of biological rhythms, many studies have also shown that biological rhythms are highly correlated with brain cognitive functions, central nervous system and neurodegenerative diseases. Accordingly, apart from deteriorating the quality of life, disorders of biological rhythms may also cause neurological disorders, and thus the regulation of biological rhythms becomes even more difficult.

In view of all this, for biological rhythm disorders, drugs are usually used in the clinical to improve or regulate biological rhythm related factors. However, long-term use or over use of drugs has become a heavy burden to the body, and may cause adverse side effects. Thus, there is a need to develop methods or devices that can improve or regulate the biological rhythm in a more natural and comfortable manner.

SUMMARY OF THE INVENTION

Technical Means for Solving the Problems

To solve the above issues, an embodiment of the present invention provides a composite intelligent biological phototherapy device. Said composite intelligent biological phototherapy device comprises a base structure, a plurality of white light fluorescent tubes, a plurality of LEDs, a housing, a light-transmittable plate and a control module. The base structure comprises a plurality of sections, and each of the plurality of sections has a first surface. The plurality of white light fluorescent tubes arranged side by side on the base structure. The plurality of LEDs are disposed between the plurality of white light fluorescent tubes along an extending direction of the plurality of white light fluorescent tubes. The housing has an opening and is configured to accommodate the base structure, the plurality of white light fluorescent tubes and the plurality of LEDs. The light-transmittable plate is disposed on the housing corresponding to the opening. The control module is configured to respectively regulate the plurality of white light fluorescent tubes and the plurality of LEDs. In the composite intelligent biological phototherapy device, the plurality of white light fluorescent tubes and the plurality of LEDs are disposed on the first surface of the plurality of sections facing the light-transmittable plate, and the plurality of sections are bent relative to each other so an angle between the first surfaces of adjacent sections is less than 180 degrees.

Technical Effects Achieved by the Technical Means

According to the composite intelligent biological phototherapy device provided by the embodiments of the present invention, a functional light with single or limited range of wavelengths can be provided in a manner similar to the natural light. Therefore, the composite intelligent biological phototherapy device can be used to regulate the biological rhythm of the user while decreasing or preventing the discomfort of the user.

BRIEF DESCRIPTION OF THE DRAWINGS

The above and further features, advantages and benefits of the present invention will be apparent upon consideration of the present description taken in conjunction with the accompanying drawings, in which.

DETAILED DESCRIPTION OF THE PRESENT INVENTION

The present invention will be described more fully hereinafter with reference to the accompanying drawings, in which exemplary embodiments of the invention are shown. In the drawings, the thickness of layers and regions may be exaggerated or otherwise modified for clarity. The same or similar reference numerals in different drawings represent the same or similar elements. Furthermore, well-known structures, materials, or operations are not shown or described in detail to avoid obscuring aspects of the described devices. As those skilled in the art would realize, the described embodiments may be modified in various different ways, all without departing from the spirit or scope of the present invention. It should be noted that, without conflict, in the embodiment of the present invention and examples of features can be combined with each other. Therefore, it should be appreciated that the embodiments described herein are not intended to be exhaustive of all possible embodiments in accordance with the present disclosure, and that additional embodiments may be conceived based on the subject matter disclosed herein.

Figure 1:
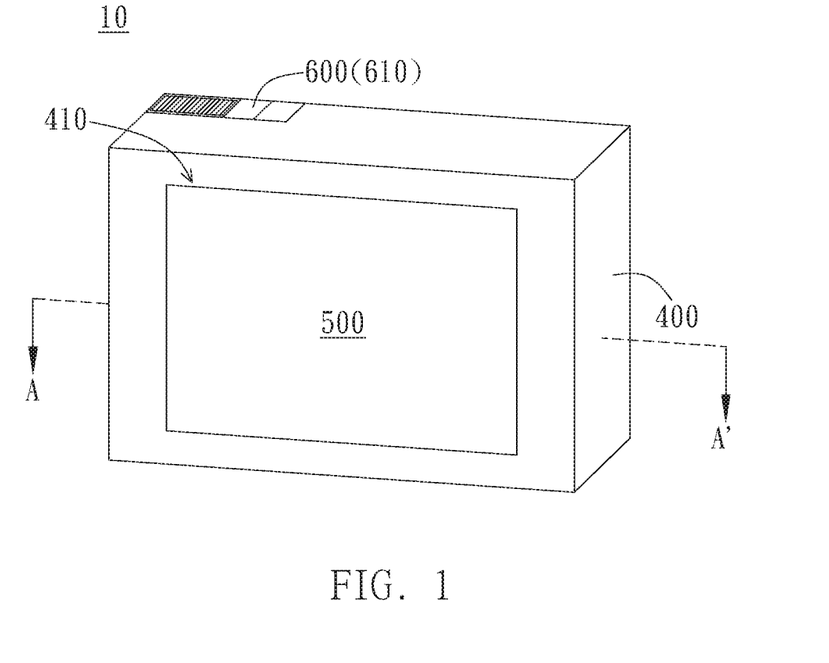
FIG. 1 is a perspective view of a composite intelligent biological phototherapy device according to an embodiment of the present invention.
Figure 2:
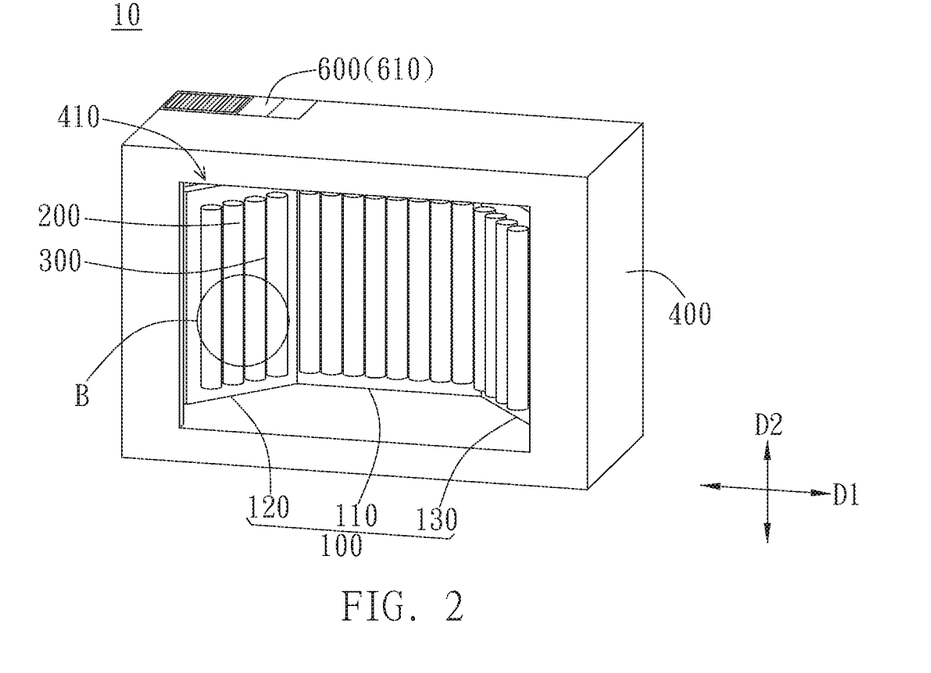
FIG. 2 is a perspective view of the composite intelligent biological phototherapy device of FIG. 1 without the light-transmittable plate.
Figure 3:
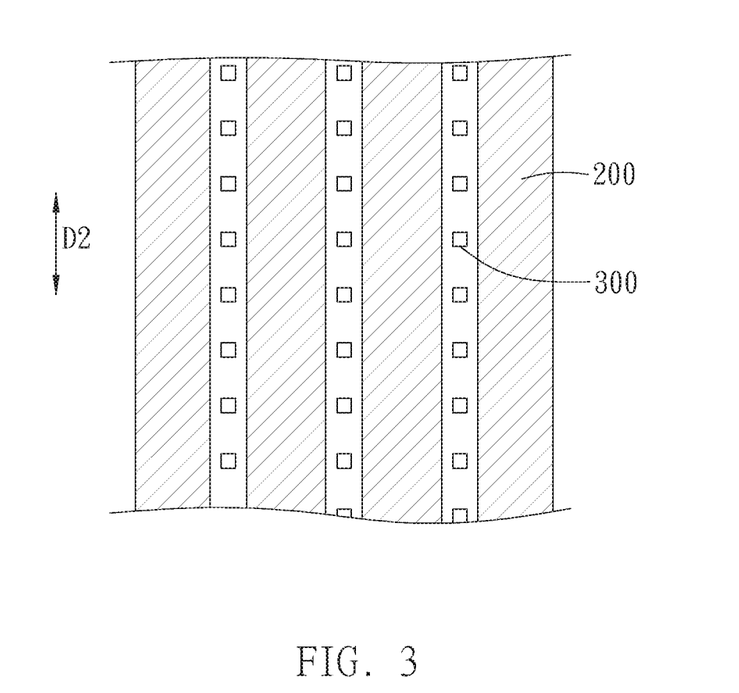
FIG. 3 is a partial enlarged view of a portion B of the composite intelligent biological phototherapy device of FIG. 2.
Figure 4:
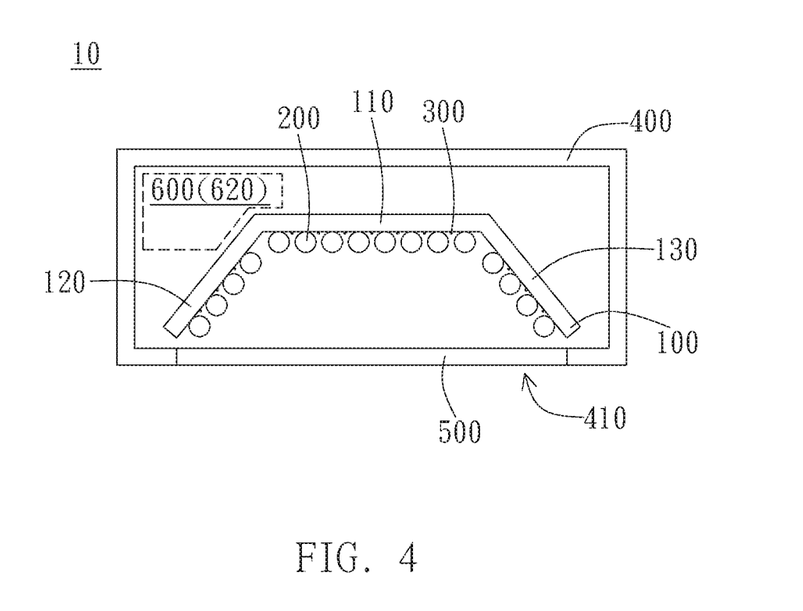
FIG. 4 is a schematic top cross-sectional view of the composite intelligent biological phototherapy device taken along the section line A-A' of FIG. 1.

Hereinafter, a composite intelligent biological phototherapy device according to an embodiment of the present invention will be described with reference to FIG. 1 to FIG. 4. FIG. 1 is a perspective view of a composite intelligent biological phototherapy device 10 according to an embodiment of the present invention; FIG. 2 is a perspective view of the composite intelligent biological phototherapy device 10 of FIG. 1 without the light-transmittable plate 500; FIG. 3 is a partial enlarged view of a portion B of FIG. 2; and FIG. 4 is a schematic top cross-sectional view of the composite intelligent biological phototherapy device 10 taken along the section line A-A' of FIG. 1.

As described above, referring to FIG. 1 and FIG. 2, according to an embodiment of the present invention, the composite intelligent biological phototherapy device 10 includes a base structure 100, a plurality of white light fluorescent tubes 200 arranged side by side on the base structure 100, a plurality of LEDs 300 arranged between the plurality of white light fluorescent tubes 200 along the extending direction of the plurality of white light fluorescent tubes 200, a housing 400 having an opening 410, a light-transmittable plate 500 disposed corresponding to the opening 410, and an control module 600 configured to respectively regulate the plurality of white light fluorescent tubes 200 and the plurality of LEDs 300. In the composite intelligent biological phototherapy device 10, referring to FIG. 1 and FIG. 2, the housing 400 is configured to accommodate the base structure 100, the plurality of white light fluorescent tubes 200, and the plurality of LEDs 300 therein. According to an embodiment of the present invention, the housing is opaque. However, the present invention is not limited thereto.

Specifically, the base structure 100 comprises a plurality of sections, and the plurality of sections are bent relative to each other. For example, referring to FIG. 2, the base structure 100 includes a first section 110, a second section 120, and a third section 130. The first section 110 is disposed parallel to the opening 410. The second section 120 and the third section 130 are respectively disposed at two sides of the first section 110 and bent with respect to the first section 110. The second section 120, the first section 110 and the third section 130 are disposed sequentially along the direction D1 and bent relative to each other, such that the overall base structure 100 has a bay window-shaped structure.

The plurality of white light fluorescent tubes 200 may be disposed in parallel on the second section 120, the first section 110 and the third section 130 of the base structure 100. In detail, the plurality of white light fluorescent tubes 200 are arranged along the direction of arrangement of the second section 120, the first section 110 and the third section 130, that is, along the direction D1 as shown in FIG. 2.

Next, referring to FIG. 3, an enlarged schematic view of portion B of FIG. 2 is shown. Specifically, in each of the first section 110, the second section 120 and the third section 130, a plurality of LEDs 300 may be disposed between white light fluorescent tubes 200. In detail, a plurality of LEDs 300 may be arranged along the extending direction D2 of the white light fluorescent tube 200 between the white light fluorescent tubes 200. In an embodiment, the direction D2 may be perpendicular to the bending and extending direction D1 of the base structure 100, but the present invention is not limited thereto. Accordingly, by arranging the white light fluorescent tubes 200 with larger volume densely and arranging the LEDs 300 with smaller volume at the gaps between the white light fluorescent tubes 200, the light emitted from the white light fluorescent tubes 200 and the LEDs 300 can be mixed. Thus, the defects such as the shadow caused by the gaps between the light sources can be reduced with such arrangement.

Here, the white light fluorescent tubes 200 emit light having a high color rendering index and having wavelengths over a wide range of wavelength band. According to a preferred embodiment of the present invention, the white light fluorescent tubes 200 emit light having wavelengths over a full wavelength band. Therefore, the white light fluorescent tubes 200 emit white light similar to the natural light.

In contrast, the LEDs 300 emit light having single or limited range of specific wavelengths. For example, red light, green light, blue light, or the like. According to an embodiment of the present invention, the plurality of LEDs 300 may include a red LED emitting red light having a wavelength of 650-680 nm, a green LED emitting green light having a wavelength of 510-535 nm, and a blue LED emitting blue light having a wavelength of 470 and 490 nm. The plurality of LEDs 300 of the present invention may be selected from the group consisting of a red LED, a green LED, a blue LED, or any combination thereof in such embodiment. However, the above is only illustrated as an example, and the color light emitted from the LED of the present invention is not limited thereto. For example, according to another embodiment of the present invention, at least one of the plurality of LEDs 300 may also include an LED 300 that emits white light. Nevertheless, although the light emitted from a white LED is also perceived as white light by the naked eye, it is different from the white light of the white light fluorescent tubes 200. In detail, the white light of the white LED is substantially a light of a single wavelength or a mix light of several specific wavelength rather than a white light over a wide wavelength band or over a full wavelength band.

As stated above, each of the plurality of LEDs 300 may be an LED of the same or different color light, respectively, and the proportions of the color LEDs may be configured according to the requirements or the purpose. For example, a blue LED can be used to disturb or adjust the sleep cycle, a green LED can achieve the similar effect of the blue LED on a blue light-resistant patient such as a patient suffering from the cataracts, and a red or white LED can be used as a soothing light source to ease and dilute the stimulation to the user from the blue or green light. Therefore, the proportion of the blue LED, the green LED, the red LED, and the white LED can be assigned in accordance with the demands or the purposes, such as interference or adjustment of the sleep cycle. However, the color light of specific wavelength used in the present invention is not limited to the specific examples stated above, and the types and the amount of the color light can be adjusted and arranged according to the demands or the purposes of the user.

According to a preferred embodiment of the present invention, the plurality of white light fluorescent tubes 200 and the plurality of LEDs 300 may be replaced respectively. That is, at least part of the plurality of white light fluorescent tubes and the plurality of LEDs are replaceable. In detail, the replacement can be performed when a single or parts of the white light fluorescent tubes 200 or the LEDs 300 is breakdown or is deteriorated, or when the light source composition needs to be changed as required and/or desired.

Further, referring to FIG. 4, which is a schematic top view of the internal structure of the composite intelligent biological phototherapy device 10 of FIG. 1 taken along the section line A-A', the base structure 100 functions in a manner similar to the light collecting cover. Accordingly, the light of the white light fluorescent tubes 200 and the LEDs 300 emit through the light-transmittable plate 500 disposed corresponding to the opening 410. Therefore, the light emitted from the white light fluorescent tubes 200 and the LEDs 300 are further mixed, so that the light emitted from the composite intelligent biological phototherapy device 10 through the light-transmittable plate 500 is presented as a light similar to the natural light. That is, although the LEDs 300 emitting the light with lower color rendering index are included, the light emitted from the composite intelligent biological phototherapy device 10 through the light-transmittable plate 500 possesses higher color rendering index than the light emitted from the plurality of LEDs 300. Thereby, the user can receive the irradiation and the treatment of the specific wavelength of light without perceiving or reducing the perception of the existence of the light with the specific wavelength.

For example, according to an embodiment of the present invention, the light emitted from the composite intelligent biological phototherapy device 10 through the light-transmittable plate 500 may be a light with wavelengths over full wavelength bands and high color rendering index. That is, a white light similar to the natural light. However, in such white light, one or several specific wavelengths account for a large proportion. In other words, one or several specific wavelengths in such white light is enhanced. Moreover, in accordance with a preferred embodiment of the present invention, the color temperature of the white light emitted from the composite intelligent biological phototherapy device 10 through the light-transmittable plate 500 may be 5500 k, such that the user feels the white light further closer to the natural light.

The above light-transmittable plate 500 may be a light-permeable plate made of acrylic, glass or the like, and may be a diffuser, so uniformity of the light emitted through the light-transmittable plate 500 is increased. However, the above is only an example, and the present invention is not limited thereto. For example, a light-transmittable plate 500 with other effects or a light-transmittable plate 500 made of other materials can also be used.

According to the above configuration, the control module 600 of the composite intelligent biological phototherapy device 10 can be configured to control many factors. For example, the switches, illuminance, relative proportion, turn-on time and irradiation duration of each of the white light fluorescent tubes 200 and the LEDs 300, and the present invention is not limited thereto.

In detail, in order to comply with the demands and the purpose of the user, the control module 600 may be used to respectively control the switches, illuminance, relative proportion, turn-on time and irradiation duration, etc. of at least parts of the white light fluorescent tubes 200 and at least parts of the LEDs. For example, if the same number of red LEDs, green LEDs, blue LEDs, and white LEDs are disposed, when there is a need to increase the blue light ratio, it can be achieved by turning on more blue LEDs and reducing the number of other color LEDs that are turn on, or increasing the luminance of the blue LEDs. However, this is only an example, and the present invention is not limited thereto.

For convenience of operation, the control module 600 may include a manipulation portion 610 disposed at the housing 400. For instance, the manipulation portion 610 can be disposed at the top of the housing 400, but the present invention is not limited thereto. Further, the manipulation portion 610 may be electrically connected to the respective white light fluorescent tubes 200 and the respective LEDs 300, and may be electrically connected to the processing circuit portion 620 of the control module 600 disposed in the composite intelligent biological phototherapy device 10. Accordingly, the user can respectively operate and control each of the white light fluorescent tubes 200 and the LEDs 300 by the control module 600 through the manipulation portion 610.

Next, referring to FIG. 5 in conjunction with FIG. 4, the bending angle of the base structure 100 in which the white light fluorescent tubes 200 and the LEDs 300 are arranged will be described.

Figure 5:
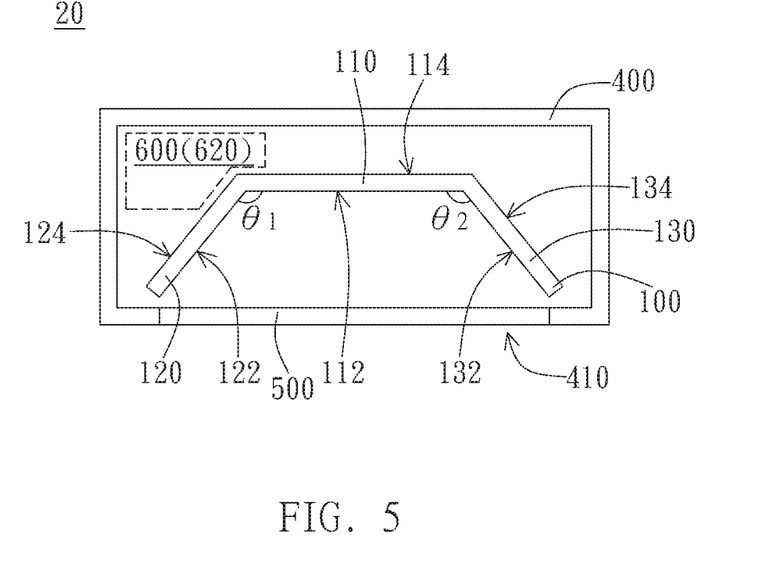
FIG. 5 is a schematic view of the bending angle of the base structure of the composite intelligent biological phototherapy device according to the first modified embodiment of the present invention.

Referring to FIG. 5, according to a first modified embodiment of the present invention, each of the plurality of sections 110 to 130 of the base structure 100 of the composite intelligent biological phototherapy device 20 has a first surface facing the opening 410 or the light-transmittable plate 500, and a second surface opposite to the first surface.

Specifically, in the case that the base structure 100 includes the first section 110, the second section 120 and the third section 130, the first section 110 may include a first surface 112 and a second surface 114, the second section 120 may include a first surface 122 and a second surface 124, and the third section 130 may include a first surface 132 and a second surface 134. The plurality of white light fluorescent tubes 200 and the plurality of LEDs 300 may be disposed on the first surfaces 112, 122, and 132 of the plurality of sections facing the light-transmittable plate 500.

As described above, the angle between the first surfaces of adjacent sections is less than 180 degrees. That is, an angle $\theta_1$ between the first surface 112 of the first section 110 and the first surface 122 of the second section 120, and an angle $\theta_2$ between the first surface 112 of the first section 110 and the first surface 132 of the third section 130 are all less than 180 degrees. For example, according to one embodiment of the present invention, the angle $\theta_1$ or $\theta_2$ may be adjusted to 135 degrees. As a result, although the overall appearance of the composite intelligent biological phototherapy device 20 is presented as a single light-emitting surface of the light-transmittable plate 500, there are substantially multiple light-emitting surfaces in the composite intelligent biological phototherapy device 20. Thereby, without reducing the irradiation dose, the irradiation angle for the user to receive the light in front of the composite intelligent biological phototherapy device 20 is widened. In this case, when the user looks at the composite intelligent biological phototherapy device 20 from one side of the composite intelligent biological phototherapy device 20, the user will not only be able to receive the oblique incident light from the light sources on the first section 110 but will also at least receive the direct incident light as the main incident light from the light sources on the second section 120 or the third section 130.

Figure 6:
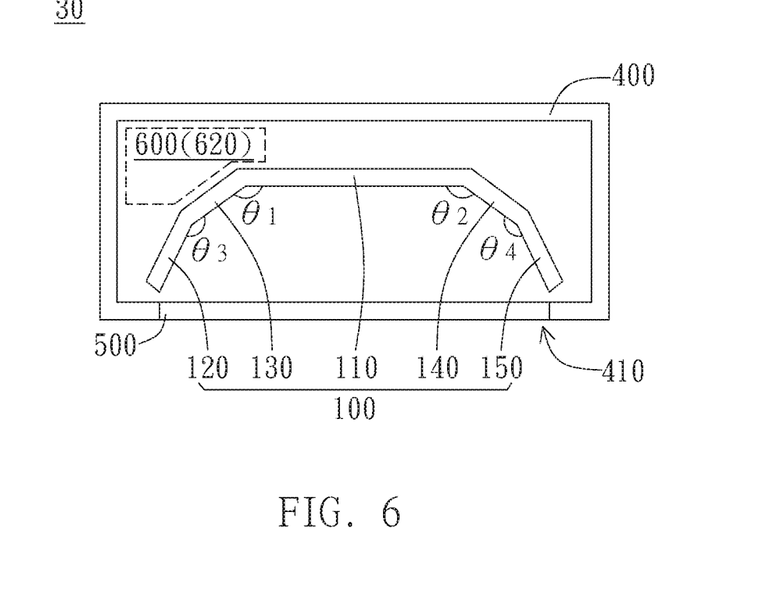
FIG. 6 is a schematic view of the bending angle of the base structure of the composite intelligent biological phototherapy device according to the second modified embodiment of the present invention.

Similarly, referring to FIG. 6, according to a second modified embodiment of the present invention, the base structure 100 may include a first section 110, a second section 120, a third section 130, a fourth section 140 and a fifth section 150. The plurality of sections 110 to 150 are bent in a manner that the base structure 100 has a bay window-shaped structure. In this case, similar to the above embodiments, the plurality of white light fluorescent tubes 200 and the plurality of LEDs 300 are disposed on the first surfaces of the plurality of sections facing the light-transmittable plate 500.

Similar to the first modified embodiment, in the composite intelligent biological phototherapy device 30 of the second modified embodiment, the angle between the first surfaces of adjacent sections may be less than 180 degrees. That is, the angle $\theta_1$ between the first surfaces of the first section 110 and the first surface of the third section 130, the angle $\theta_2$ between the first surfaces of the first section 110 and the first surface of the fourth section 140, the angle $\theta_3$ between the first surface of the third section 130 and the first surface of the second section 120, and the angle $\theta_4$ between the first surface of the fourth section 140 and the first surface of the fifth section 150 are all less than 180 degrees. For example, according to one embodiment of the present invention, the angles $\theta_1$, $\theta_2$, $\theta_3$, and $\theta_4$ may be adjusted to 135 degrees. As a result, although the overall appearance of the composite intelligent biological phototherapy device 30 is presented as a single light-emitting surface of the light-transmittable plate 500, there are substantially multiple light-emitting surfaces in the composite intelligent biological phototherapy device 30. Thereby, without reducing the irradiation dose, the irradiation angle for the user to receive the light of the white light fluorescent tubes 200 and the LEDs 300 in front of the composite intelligent biological phototherapy device 30 is widened.

According to a preferred embodiment of the present invention, the angles between the first surfaces of adjacent sections of the plurality of sections as shown in FIG. 5 and FIG. 6 are adjustable, and the adjustment can be performed in accordance with variety factors. For example, the location of the user.

Figure 7:
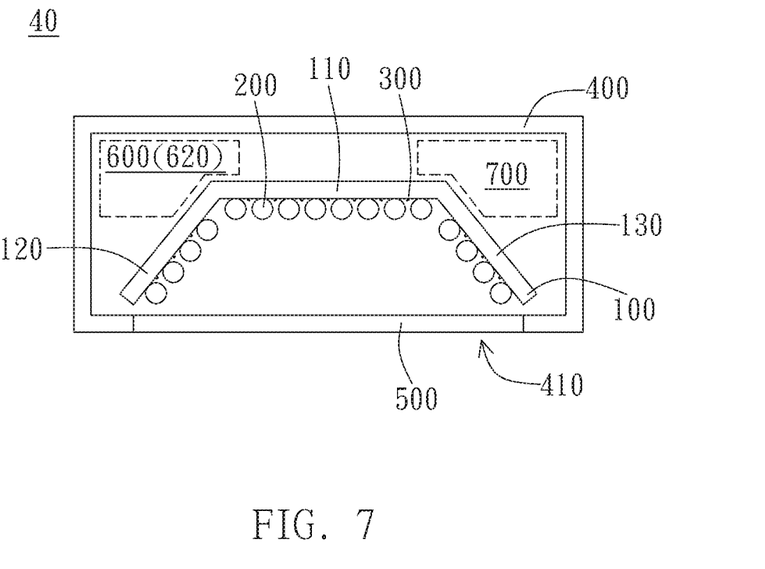
FIG. 7 is a schematic top cross-sectional view of the composite intelligent biological phototherapy device according to the third modified embodiment of the present invention.

Next, referring to FIG. 7, the composite intelligent biological phototherapy device 40 according to the third modified embodiment of the present invention will be further described.

As shown in FIG. 7, the difference between the composite intelligent biological phototherapy device 40 according to the third modified embodiment of the present invention and the composite intelligent biological phototherapy device 10 shown in FIG. 4 is that the composite intelligent biological phototherapy device 40 further comprises a data recording module 700.

Specifically, the data recording module 700 is configured to record the respective irradiation data of the plurality of white light fluorescent tubes 200 and the plurality of LEDs 300. The irradiation data includes the type, switch, illuminance, relative proportion, turn-on time and irradiation duration of the plurality of white light fluorescent tubes 200 and the plurality of LEDs 300, but is not limited thereto. These irradiation data may be used to feedback control the composite intelligent biological phototherapy device 40 (for example, provide feedback for the control module 600), or may be provided to the user or other related personnel for analysis. Accordingly, the specific physiological adjustment and/or effect can be confirmed and adjusted in accordance with the irradiation data. Thus, it is easier to use and adjust the composite intelligent biological phototherapy device 40 for improving the physical and mental health of a subject.

Hereinafter, composite intelligent biological phototherapy devices according to other modified embodiments of the present invention will be described.

Figure 8:
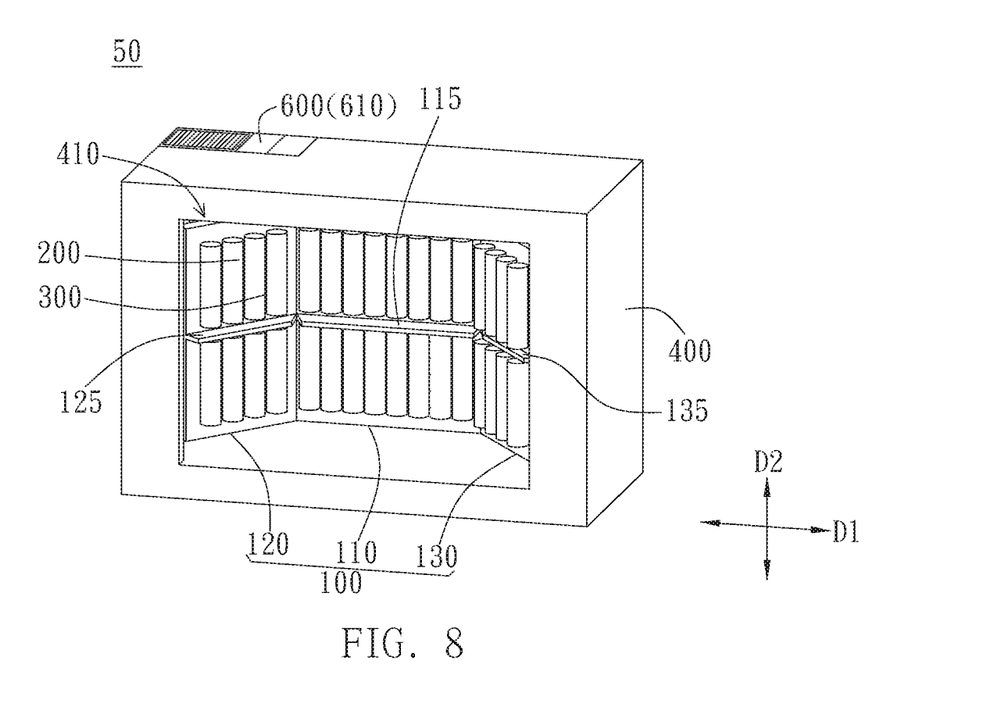
FIG. 8 is a perspective view of the composite intelligent biological phototherapy device according to the fourth modified embodiment of the present invention.

Referring to FIG. 8, in a composite intelligent biological phototherapy device 50 according to the fourth modified embodiment of the present invention, each of the plurality of sections 110 to 130 of the base structure 100 may be further divided into different regions. For example, the first section 110 may be further divided into an upper region and a lower region separated by the first partition block 115, the second section 120 may be further divided into an upper region and a lower region separated by the second partition block 125, and the third section 130 may be further divided into an upper region and a lower region separated by the third partition block 135. However, it should be noted that the above is only illustrated as examples, and the base structure 100 of the composite intelligent biological phototherapy device according to other embodiments of the present invention may be divided into several regions without partition blocks. That is, the composite intelligent biological phototherapy device 50 may not include one or more of the first partition block 115, the second partition block 125, and the third partition block 135.

The plurality of white light fluorescent tubes 200 can be respectively arranged in the upper region and the lower region in separate rows. For example, as shown in FIG. 8, two rows of white light fluorescent tubes 200 may be arranged along the direction D2, and a plurality of LEDs 300 with different color light may be disposed between adjacent white light fluorescent tubes 200 as described above. On this ground, the freedom of arranging different types and numbers of white light fluorescent tubes 200 and the LEDs 300 can be increased, thereby increasing the variation of the light emitted from the plurality of white light fluorescent tubes 200 and the plurality of LEDs 300.

Figure 9:
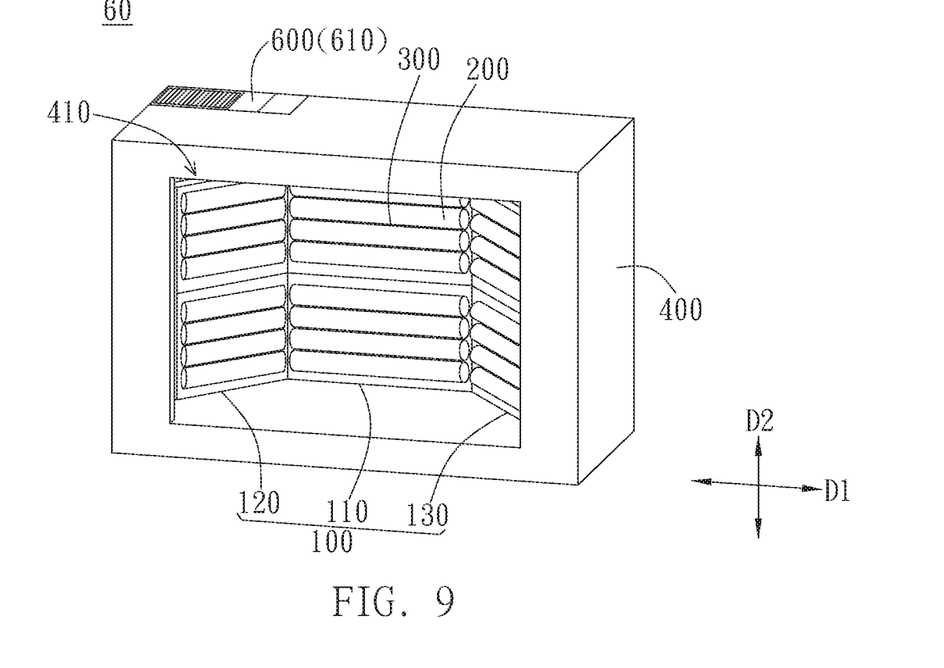
FIG. 9 is a perspective view of the composite intelligent biological phototherapy device according to the fifth modified embodiment of the present invention.

Next, a composite intelligent biological phototherapy device 60 according to the fifth modified embodiment of the present invention will be described with reference to FIG. 9.

In the above composite intelligent biological phototherapy devices as described with reference to FIG. 1 to FIG. 8, the plurality of white light fluorescent tubes 200 are mainly arranged along the bending and extending direction D1 of the base structure 100 and are extended along the direction D2. However, the present invention is not limited thereto. For example, referring to the composite intelligent biological phototherapy device 60 shown in FIG. 9, the plurality of white light fluorescent tubes 200 may also be arranged in a matrix form along the direction D1 and D2 and are extended along the direction D1. In addition, in this example, since the first section 110, the second section 120 and the third section 130 are bent with respect to each other, three columns of the white light fluorescent tubes 200 arranged along the direction D2 can be disposed respectively on the three sections.

As mentioned above, in the case that a plurality of white light fluorescent tubes 200 are arranged densely and a plurality of LEDs 300 are disposed between the white light fluorescent tubes 200, the manner and the pattern for arranging the white light fluorescent tubes 200 on the base structure 100 can be varied. For example, the configuration, the numbers of rows/columns and the amount in each row/column of the white light fluorescent tubes 200 and the LEDs 300 therebetween can be adjusted in accordance with the configuration of wires or elements associated with the control module 600 and/or the data recording module 700 and/or other devices as desired. That is, the arrangement of the white light fluorescent tubes 200 and the LEDs 300 can be assigned in accordance with the degree of control freedom as desired, and the present invention is not limited to the examples stated in the specification. That is, in the case that the light emitted from the composite intelligent biological phototherapy device through the light-transmittable plate 500 satisfy the expect degree of uniformity, the configuration, the numbers of rows/columns and the amount in each row/column of the white light fluorescent tubes 200 and the LEDs 300 therebetween may be varied.

Figure 10:
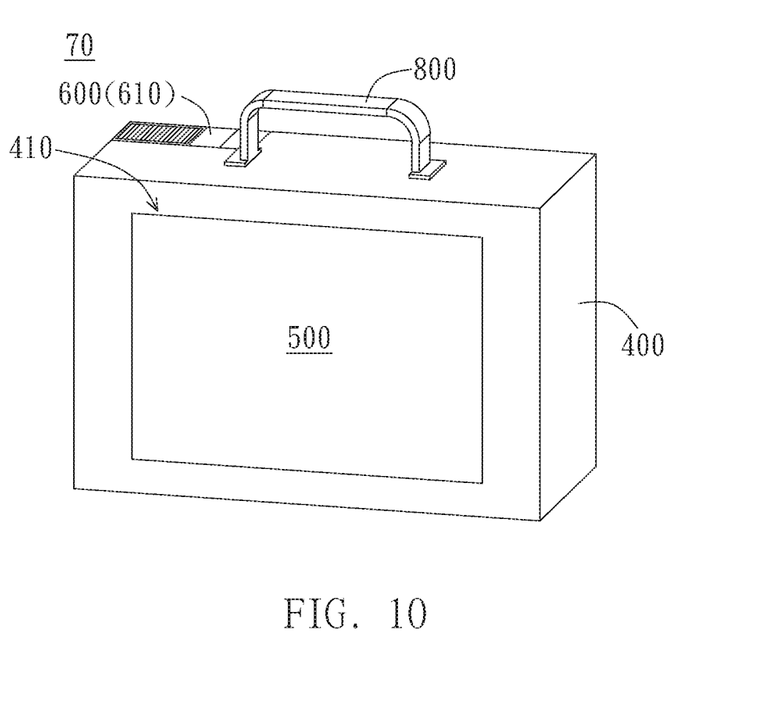
FIG. 10 is a perspective view of the composite intelligent biological phototherapy device according to the sixth modified embodiment of the present invention.

Further, referring to FIG. 10, according to the composite intelligent biological phototherapy device 70 according to the sixth modified embodiment of the present invention, a handle 800 may be further disposed on the housing 400. Therefore, the portability and the freedom to adjust the irradiation angle of the composite intelligent biological phototherapy device 70 can be increased, thereby improving the applicability and the convenience of the composite intelligent biological phototherapy device 70.

It should be noted that the form of the handle 800 shown herein is only an example, and the present invention is not limited thereto.

To sum up, the composite intelligent biological phototherapy devices according to various embodiments of the present invention combine the fluorescent light source with high color rendering index and the LED light source with specific functional wavelength, such that the adjustment of the biological rhythms can be performed by the composite intelligent biological phototherapy device of the present invention in accordance with various situations, demands or expectation. For example, the user may be able to improve the synchronization of the wake cycle with the activity duration of a day, or improve insomnia or dementia or other mental and physical problems by adjusting the sleep cycle. Thus, the composite intelligent biological phototherapy devices of the present invention can be used to take care of the mental and physical conditions of the user while reducing the stimulation and burden to the user. Accordingly, the individual health and the life quality of the user of the composite intelligent biological phototherapy device can be further improved.

Although the present invention has been described with reference to the preferred embodiments thereof, it will be understood that the invention is not limited to the details thereof. Various changes and modifications in accordance with the appropriate technical solutions and technical concepts of the present invention should belong to the invention as claimed. Therefore, all such substitutions and modifications are intended to be embraced within the scope of the invention as defined in the appended claims.

What is claimed is:

1. A composite intelligent biological phototherapy device, comprising:
   a base structure comprising a plurality of sections, each of the plurality of section having a first surface;
   a plurality of white light fluorescent tubes arranged side by side on the base structure;
   a plurality of LEDs disposed between the plurality of white light fluorescent tubes along an extending direction of the plurality of white light fluorescent tubes;
   a housing having an opening, the housing configured to accommodate the base structure, the plurality of white light fluorescent tubes and the plurality of LEDs;
   a light-transmittable plate disposed on the housing corresponding to the opening; and
   a control module configured to respectively regulate the plurality of white light fluorescent tubes and the plurality of LEDs;
   wherein the plurality of white light fluorescent tubes and the plurality of LEDs are disposed on the first surfaces of the plurality of sections facing the light-transmittable plate, and the plurality of sections are bent relative to each other so an angle between the first surfaces of adjacent sections is less than 180 degrees.

2. The composite intelligent biological phototherapy device of claim 1, wherein the plurality of LEDs comprise at least one of a red LED, a green LED, and a blue LED.

3. The composite intelligent biological phototherapy device of claim 2, wherein a red light emitted from the red LED has a wavelength of 650-680 nm, a green light emitted from the green LED has a wavelength of 510-535 nm, and a blue light emitted from the blue LED has a wavelength of 470-490 nm.

4. The composite intelligent biological phototherapy device of claim 1, wherein a light emitted from the composite intelligent biological phototherapy device through the light-transmittable plate is a white light.

5. The composite intelligent biological phototherapy device of claim 4, wherein a color temperature of the white light emitted from the composite intelligent biological phototherapy device through the light-transmittable plate is 5500 k.

6. The composite intelligent biological phototherapy device of claim 1, wherein a light emitted from the composite intelligent biological phototherapy device through the light-transmittable plate has a higher color rendering index than a light emitted from the plurality of LEDs.

7. The composite intelligent biological phototherapy device of claim 1, further comprising a data recording module configured to record respective irradiation data of the plurality of white light fluorescent tubes and the plurality of LEDs.

8. The composite intelligent biological phototherapy device of claim 1, wherein the angle between the first surfaces of the adjacent sections of the plurality of sections is adjustable.

9. The composite intelligent biological phototherapy device of claim 1, wherein the angle is 135 degrees.

10. The composite intelligent biological phototherapy device of claim 1, wherein the plurality of sections are bent in a manner that the base structure has a bay window-shaped structure with at least two bends.

11. The composite intelligent biological phototherapy device of claim 1, wherein the light-transmittable plate is a diffuser, so uniformity of the light emitted through the light-transmittable plate is increased.

12. The composite intelligent biological phototherapy device of claim 1, wherein the light-transmittable plate is made of acrylic or glass.

13. The composite intelligent biological phototherapy device of claim 1, wherein each of the plurality of sections of the base structure is divided into a plurality of regions, and the plurality of white light fluorescent tubes are respectively arranged in the plurality of regions in separate rows or columns.

14. The composite intelligent biological phototherapy device of claim 13, further comprising a partition block disposed between the regions.

15. The composite intelligent biological phototherapy device of claim 1, further comprising a handle disposed on the housing.

16. The composite intelligent biological phototherapy device of claim 1, wherein the plurality of white light fluorescent tubes are arranged on the plurality of sections sequentially disposed along a first direction, and the extending direction of the white light fluorescent tubes is perpendicular to the first direction.

17. The composite intelligent biological phototherapy device of claim 1, wherein the plurality of white light fluorescent tubes are arranged on the plurality of sections sequentially disposed along a first direction, and the extending direction of the white light fluorescent tubes is parallel to the first direction.

* * * * *